United States Patent
Ebert et al.

(10) Patent No.: US 8,849,728 B2
(45) Date of Patent: Sep. 30, 2014

(54) VISUAL ANALYTICS LAW ENFORCEMENT TOOLS

(75) Inventors: David S. Ebert, West Lafayette, IN (US); Timothy Collins, Brookston, IN (US); Ross Maciejewski, West Lafayette, IN (US); Abish Malik, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 139 days.

(21) Appl. No.: 13/291,761

(22) Filed: Nov. 8, 2011

(65) Prior Publication Data
US 2013/0057551 A1    Mar. 7, 2013

Related U.S. Application Data

(63) Continuation-in-part of application No. 13/190,748, filed on Jul. 26, 2011, which is a continuation-in-part of application No. 12/286,756, filed on Oct. 1, 2008, now abandoned.

(60) Provisional application No. 61/411,447, filed on Nov. 8, 2010, provisional application No. 60/997,150, filed on Oct. 1, 2007.

(51) Int. Cl.
*G06F 15/18* (2006.01)
*G06K 9/62* (2006.01)
*G06F 19/00* (2011.01)

(52) U.S. Cl.
CPC .................... *G06K 9/6218* (2013.01); *G06F 19/3493* (2013.01)
USPC .......................................................... 706/12

(58) Field of Classification Search
USPC ............................................... 706/12, 45, 62
See application file for complete search history.

(56) References Cited

U.S. PATENT DOCUMENTS

2013/0031041 A1 * 1/2013 Maciejewski et al. .......... 706/46

OTHER PUBLICATIONS

Malik, A., Maciejewski, R., Collins, T. F., & Ebert, D. S., Visual analytics law enforcement toolkit, Nov. 2010. In Technologies for Homeland Security (HST), 2010 IEEE International Conference on (pp. 222-228). IEEE.*
Maciejewski, R., Hafen, R., Rudolph, S., Larew, S. G., Mitchell, M. A., Cleveland, W. S., & Ebert, D. S. (2011). Forecasting Hotspots—A Predictive Analytics Approach, 2011. Visualization and Computer Graphics, IEEE Transactions on, 17(4), 440-453.*

* cited by examiner

*Primary Examiner* — David Vincent
(74) *Attorney, Agent, or Firm* — Maginot, Moore & Beck, LLP

(57) ABSTRACT

A system and method for visually displaying and analyzing criminal and/or public health and safety data for geospatial and/or time variations, including the collection of incident data coupled with geographic and time data, filtering the symptom data based upon a selected time period and geographic range, and creating a visual result based upon statistical modeling including power transform and/or data normalization. According to at least one embodiment, the system for visually displaying and analyzing includes selecting and performing at least one aberration detection method and displaying the result to a user via a visual analytics arrangement.

15 Claims, 6 Drawing Sheets

VISUAL ANALYTICS LAW ENFORCEMENT TOOLS

PRIORITY

This application claims priority to of Provisional U.S. Patent Application Ser. No. 61/411,447, entitled "Visual Analytics Law Enforcement Toolkit", filed Nov. 8, 2010, as well as U.S. patent application Ser. No. 13/190,748 to Ebert et al., entitled "Linked Animal-Human Health Visual Analytics", filed Jul. 26, 2011, which is a continuation-in-part of U.S. patent application Ser. No. 12/286,756 to Ebert et al. and entitled "Linked Animal-Human Health Visual Analytics, filed Oct. 1, 2008, now abandoned, which claimed the benefit of U.S. Provisional Patent Application Ser. No. 60/997,150, filed Oct. 1, 2007, each of which are incorporated herein by reference.

This invention was made with Government support under 2009-ST-061-CI0001 awarded by Deparment of Homeland Security. The Government has certain rights in the invention.

FIELD OF THE INVENTION

The present invention relates generally to visual analytic tools, and more particularly, to visual analytic tools used in the field of public safety.

BACKGROUND OF THE INVENTION

The role of law enforcement and public safety programs is to ensure compliance with the law and to maximize public health and safety with a finite number of resources. In order to improve public safety and prevent crimes, law enforcement agencies have begun analyzing volumes of data from multiple systems, searching for trends to help predict the likelihood of future criminal activity in a particular area during a specified time.

The exploration of criminal incident reports for detecting trends, discovering anomalies and evaluating resource usage is an ever expanding issue for law enforcement agencies. It is no longer efficient for a single analyst to pull files, take notes, form hypotheses and request data from different sources. Further, as budgets shrink and departments scale back, the ability of local law enforcement agencies to effectively analyze the data being collected becomes increasingly strained. As such, tools need to be developed that bring varying data sources into a unified framework assisting analysis and exploration in order to speed the analytical process and ease the burden on local agencies.

Many of these tool development needs are being explored by the emergence of a new scientific field, visual analytics. Visual analytics is the science of analytical reasoning assisted by interactive visual interfaces. However, the raw data relating to law enforcement and public health and safety can be difficult to assess or pull together into a unified picture, let alone to predict future needs. Software-based visual analytic tools have been introduced to provide displays of the symptom data in an intuitive way that may be used to identify problem areas, and may include visual analytic tools. The goal of such tools is to provide an intuitive overview of large amounts of data, preferably with the ability to drill down into the data and/or perform additional statistical analysis on select portions of the data.

In the field of law enforcement and health and safety, a user may view instances of violent crimes in a particular geographical area for various times during the year, noting times of year and/or geographic areas when the violent crimes occurred in seemingly larger numbers. The user may then perform statistical analysis to determine further information about those specific instances. However, those systems typically are not capable of both high true positive rates (precision) and low false positive rates (recall). As such, while packages exist for studying spatial relationships between crime and area demographics, including exploratory spatial data analysis to visualize spatial distributions and suggest clusters and hotspots, data sharing and crime analysis via the web, chloropleth mapping, and capability to export records to Excel, it would be appreciated if statistical tools and dynamically linked views allowed for better predictive models. Further, many systems make it difficult to accurately reflect the geographical location of a high rate violent crime area, which may be bounded by physical landmarks such as rivers, buildings, mountains, etc.

Accordingly, there is a need for improved techniques of generating and displaying visual analytics of law enforcement and public health and safety occurrences, and accurately predicting future occurrences.

SUMMARY

At least some embodiments of the present invention include a system and method comprising: obtaining first data regarding criminal, traffic and/or civil incidents, the first data comprising reported criminal, traffic and/or civil incidents from a plurality of locations; sorting the first data based upon incident categories; applying seasonal trend decomposition with loess smoothing for the first data; plotting incidents within the first data as points, density estimated heatmaps, or chloropleth maps for a defined geotemporal unit; and displaying the plotted incidents to a user via a graphic user interface.

The above-described features and advantages, as well as others, will become more readily apparent to those of ordinary skill in the art by reference to the following detailed description and accompanying drawings.

DETAILED DESCRIPTION

The present application relates to a system of analytical tools coupled with an interactive visual interface for data exploration and analysis, and a method for applying analytics to law enforcement and/or public safety data to aid in the prediction of potential trouble spots and/or times where public safety issues, criminal activity, or other potential events of concern to officials are likely to occur. According to at least one embodiment, the present system and method includes a visual analytics tool that includes linked views and interactive displays that spatiotemporally model criminal, traffic and/or civil (hereinafter, "CTC") incidents that can be modeled and displayed in a way to allow officials to observe patterns and quickly identify regions with varying probabilities of CTC activity. According to certain aspects, the present system and method provides users with the ability to visualize different types of data sets, including census data, daily weather reports, zoning tracts, prominent calendar dates, etc. that provide an insight into correlations among CTC incidents and spatial demographics.

Further, according to certain embodiments, the present system and method includes a kernel density estimation mapping technique that creates a color map of spatially distributed CTC events that allows analysts to quickly find and identify areas with unusually large activity levels. Optionally, in certain embodiments, reports can be aggregated by day, week, month or year, allowing the user to visualize CTC activities geospatially over a period of time. Furthermore, in certain embodiments the present system and method includes temporal prediction algorithms to forecast future CTC incident levels within a confidence interval of at least 95%. Such predictions aid users such as law enforcement officials in understanding how hotspots may grow in the future in order to judiciously allocate resources and take preventive measures.

Further, according to certain embodiments, the present system and method includes multi-level aggregate views for crime mapping including census tract based chloropleth maps and kernel density estimate heat maps. Additionally, certain optional embodiments include linked interactive displays for multi-domain/multivariate exploration and analysis. According to additional optional embodiments, the present system and method includes seasonal trend decomposition modeling for temporal trend analysis and prediction, and can include multiple time series views for time series exploration and trend analysis including line graphs and calendar views. Further, according to certain optional embodiments, the present system and method optionally includes crime clustering based on spatial autocorrelation and/or filter controls that enable database querying and analysis through a graphical interface.

According to certain embodiments, providing linked environments of geospatial data and time series graphs is accomplished, allowing hotspots found in one data display visualization to be selected and immediately analyzed in a corresponding linked view. Further, according to certain embodiments, the present system and method allows a user to integrate additional data streams, including community events (such as local football games), weather, and other signals of interest. As such, the present system and method allows users to look for patterns in both the spatial and temporal data domains along several data collections. Knowledge extracted here can be used to develop hypotheses and future analytic capabilities that provide means for hypothesis testing on data clusters and time series anomalies.

Figure 1:
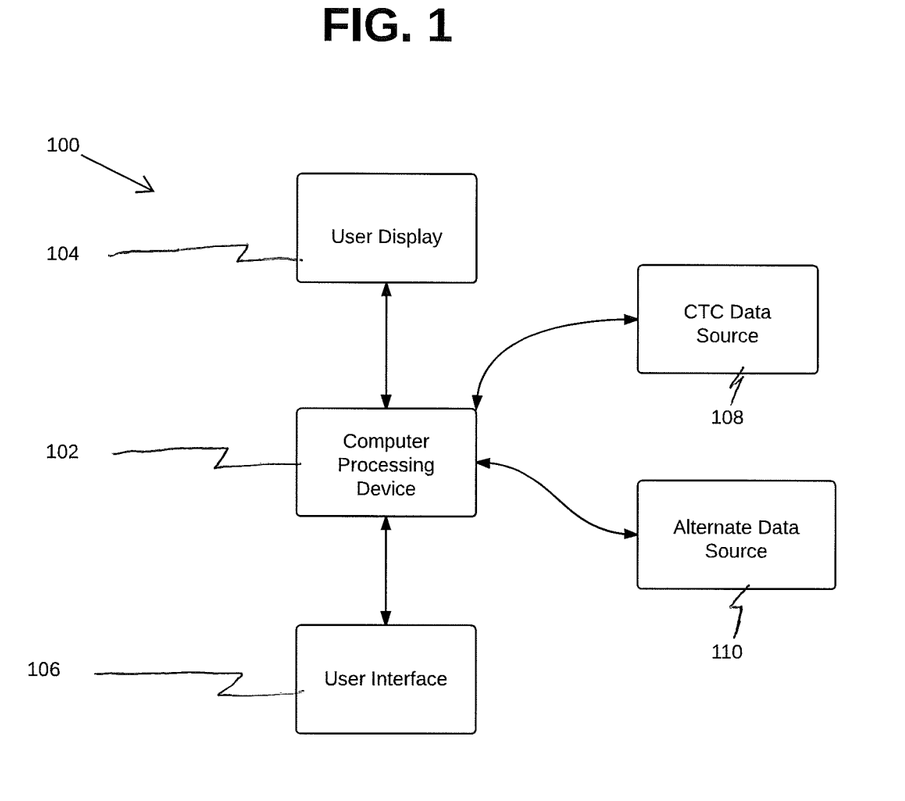
FIG. 1 shows a diagrammatic representation of a visual analytics arrangement according to an exemplary embodiment of the invention.

FIG. 1 shows a diagrammatic representation of a visual analytics arrangement 100 according to an exemplary embodiment of the invention. The visual analytics arrangement 100 includes a computer processing and storage device 102 coupled to a user display 104, a user interface 106, a CTC data source 108 and, optionally, an additional data source 110. The computer processing and storage device 102 may be any suitable work station, portable computer, or similar device. According to certain exemplary embodiments, computer processing and storage device 102 includes a network connection 112 that facilitates connection to one or more CTC data sources 108 and/or one or more additional data sources 110. Additional data source 110 is any source of past and predicted occurrences or data for a locality. By way of nonlimiting example, one current source of such data is a database from the U.S. Census Bureau, providing statistical information regarding a particular region. However, it will be appreciated that other data sources 110, including localized, regionalized, and/or nationalized reporting sources may be utilized.

User display 104 is any visual display, and may suitably comprise a display integral to or configured for the computer processing and storage device 102. Similarly, the user input device 106 may include any and all input devices normally associated with computer processing and storage devices, and indeed may comprise devices integrally packaged with the computer processing and storage device 102.

CTC data source 108 is a source of reported crime and/or health and safety occurrences coupled to a geographic location. For instance, according to at least one exemplary embodiment, CTC data source 108 is a reported list of local, national, or regional reported activity maintained by a police, emergency response, or other health and safety or related department that is optionally aggregated into different categories including: armed aggravated assault, armed robbery, burglary, homicide, noise, other assaults, rape, attempted rape, residential entry, robbery, theft, unarmed aggravated assault, vandalism and vehicle theft. According to certain embodiments, the CTC data may begin several years before the current year to provide data for seasonal and trending results. Updates may be ingested monthly within in a geographical area of interest or for all areas in which the data is available.

Figure 4:
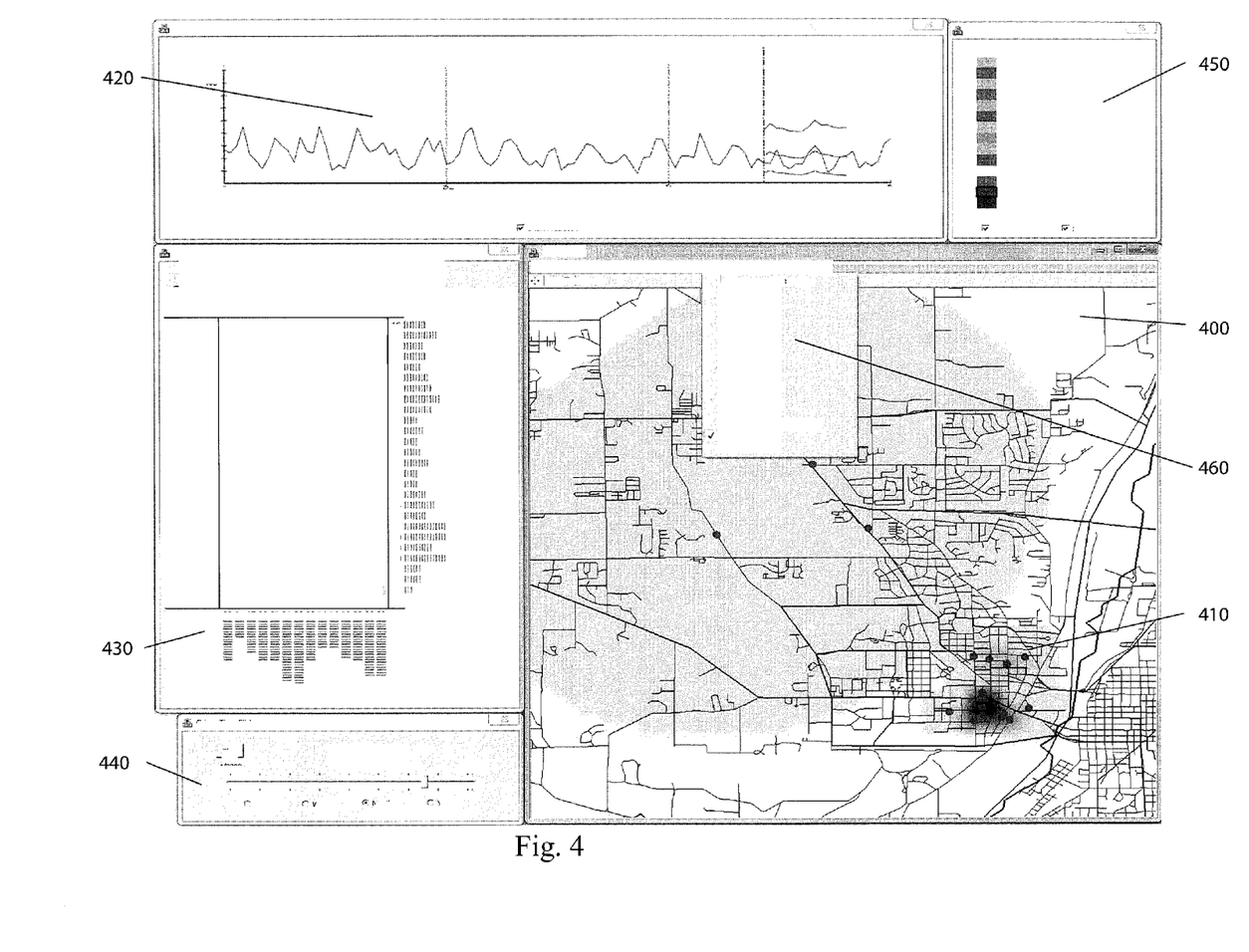
FIG. 4 shows an exemplary display generated by the visual analytics system according to one embodiment.

According to at least one exemplary embodiment, as shown in FIG. 4, a visual analytics system utilizes both data-management and statistical modeling embodiments discussed in further detail below. For instance, an initial direct access query is made, and CTC data are displayed on an interactive map such as that shown in FIG. 4. As shown in FIG. 4, at least one exemplary embodiment includes a visual display of a the geospatial rendition of temporal data 400 for a selected CTC that supports the overlay of different maps and CTC incidents along with interactive panning and zooming tools. In particular, in FIG. 4, reported CTC events 410 are depicted by a color coded circle at the location of the reported incident, with the color correlating to the category of CTC event reported. Hotspots can be shown by darkened zones on the map, with darker colors indicating higher incidences of occurrence within the area or higher probability of future incidences for all or only a category of CTC events/incidents. According to at least one exemplary embodiment, for a selected category of events, the size and color of the visual depictions directly relate to the number of cases or severity of cases seen within a selected time period, normalized by either a six-month sliding window as discussed above, or through a power transformation.

Additionally, the time series view box 420 displays a line graph time series view of the CTC data which provides users with the option of viewing the aggregate of all the selected CTC categories by type or visualizing them separately on one graph. Additionally, the calendar view box 430 of the selected CTC incidents displays the sum of crime incidents for each day of a calendar year, or for the selected time period. The calendar view box enables the users to visualize special events like football and basketball games on the calendar, further allowing them to make a connection between the reported CTC activities and any specific events. Time selection box 440 includes a time slider that is used to temporally scroll through the CTC data while dynamically updating all the other linked windows to reflect the change. Additionally, time selection box 440 optionally contains radio buttons to select the type of temporal aggregation for the CTC incidents. Finally, according to at least one embodiment, the visual analytics system includes a legend 450 depicting the color code for each of the CTC incident categories with those selected for visualization highlighted.

It will be appreciated that in at least certain embodiments, the present system includes an interactive demographic and CTC filtering component. Users interactively generate data search queries through the use of check boxes and edit controls to find specific CTC categories. This interaction is shown in the drop-down menu 460 of FIG. 4. Other filter options (using a census data menu) allow users to plot demographic data on the map, such as median income. This allows users to interactively select various data layers and search for potential correlations. Such interaction furthers hypothesis generation and exploration as users can quickly filter signals by demographic constraints in order to see if crimes are related to a particular segment of the population. The choices of filters affect both the geo-spatiotemporal viewing area and all unlocked temporal plots. Other optional system features include making legend 450 interactive. For example, by clicking on any of these selected CTC categories on the legend, the system fills the CTC circles with a solid color and further dims out the other CTC categories on the map. This action spatially highlights the selected CTC categories among all the other CTC categories selected for visualization.

Additionally, along with the advanced graphical interface, the present system contains a variety of optional visualization features for both spatial and temporal views. For temporal views, three options are provided to the user: the calendar view, the line graph view, and a predictive overlay on the line graph view. These are discussed in further detail below.

The calendar view visualization provides a means of viewing data over time, where each date is shaded based on the overall yearly trends. Here, the max data value is shaded the darkest color, and the lowest data values are shaded a light color. Users can interactively control the cycle length of the calendar view. In FIG. 4, the user has interactively chosen a cycle length of 14 days as shown in calendar view box 430. Each row and column of the calendar view also maps to a histogram plot at the bottom and right edges of the calendar. This allows users to search for both seasonal and cyclical trends. Furthermore, the present system and method also allows for multi-source data integration, including factors as weather, school calendars, local sporting events, etc., as shown by the radio buttons displayed in calendar view box 430.

Furthermore, the line graph visualization allows the user to view the temporal data trends of multiple crime signals at a single time in time view box 420. For example, if a user selects both theft and vandalism, two line graphs would appear on the map, allowing the analyst to compare trends. A user may then interactively choose to combine the input signals together using the radio button found on the time series box 420. This allows for a variety of ways to view the data. Furthermore, the data is plotted based on the time slider control in the time control box 440. In the example displayed in FIG. 4, the data is being plotted by month. Finally, the line graph view also utilizes a predictive analysis metric in order to capture trends and inform analysts of potential future issues.

Further, according to certain embodiments, in order to more accurately model data, a strategy is employed in which the time series is viewed as the sum of multiple components of variation. Seasonal-trend decomposition based on loess (locally weighted regression) is optionally used to separate the time series into its various components. In at least one embodiment, STL components of variation arise from smoothing the data using moving weighted-least squares polynomial fitting, in particular loess, with a moving window bandwidth in days, weeks, or months. The degree of the polynomial is 0 (locally constant), 1 (locally linear), or 2 (locally quadratic).

It is important to note that in order to appropriately model a time series using STL, the mean and variance of the data should be independent. According to at least one exemplary embodiment, this is performed via, a power transformation applied to the data. In time series analysis, the logarithm transformation may be applied when the mean is proportional to the standard deviation. In cases where data consists of counts following a Poisson distribution, a square root transformation can make the mean independent of the standard deviation.

According to yet another embodiment, for a given time series, data can be decomposed into a day-of-the-week component, a yearly-seasonal component that models seasonal fluctuations, and/or an inter-annual component which models long term effects. According to one embodiment, such a decomposed data is expressed as:

$$\sqrt{Y_t}=T_t+S_t+D_t+r_t$$

where for the t-th day, $Y_t$ is the original series, $T_t$ is the interannual component, $S_t$ is the yearly-seasonal component, $D_t$ is the day-of-the-week effect, and $r_t$ is the remainder. The procedure begins by extracting the day-of-the-week component, $D_t$. First, a low-middle frequency component is fitted using locally linear fitting. Then $D_t$ is the result of means for each day-of-the-week of the $Y_t$ minus the low-middle-frequency component. Next, the current $D_t$ is subtracted from the $Y_t$ and the low-middle-frequency component is re-computed. This iterative process is optionally continued until convergence. After removing the day-of-the-week component from the data, loess smoothing is optionally used to extract the interannual component, $T_t$. Finally, loess smoothing is optionally used to smooth the data with the day-of-week and inter-annual components removed, thereby obtaining the yearly-seasonal component, $S_t$, using local quadratic smoothing. After removing the day-of-week, inter-annual, and yearly-seasonal components from the time series, the remainder is found to be adequately modeled as independent identically distributed Gaussian white noise, indicating that all predictable sources of variation have been captured in the model.

For prediction using the STL method, statistical properties of loess are optionally incorporated, namely that the fitted values $\hat{Y}=(\hat{Y}_1, \ldots, \hat{Y}_n)$ are a linear transformation of the observed data, $Y=(Y_1, \ldots, Y_n)$. Each step of the STL decomposition involves a linear filter of the data. In other words, an output time series $x=\{x_1, \ldots x_n\}$ is produced by an input time series $w=w_1, \ldots, w_n$ through a linear combination:

$$x_i = \Sigma_{j=1}^{n} h_{ij} w_j.$$

If H is matrix whose (i,j)-th element is $h_{ij}$, then $x=H_w$. Further details of utilizing STL for prediction can be extended within this method to use with CTC data.

Turning back to FIG. 4, the predicted rates are plotted within the time series line, with the upper and lower confidence bounds plotted in a contrasting line. This prediction is then optionally compared to the actual data. In this example, it can be seen that the data falls within the confidence interval provided and the rises and falls of the data are relatively well captured.

Along with the various temporal viewing and analysis algorithms as disclosed herein, the present system and method optionally further provides users with various spatial mapping and analysis components. For instance, as shown in FIG. 4, the geospatial rendition of temporal data 400 allows a user to plot incidents as points, density estimated heatmaps, or chloropleth maps using census tract boundaries. For the density estimated heatmaps, a variable kernel method is optionally employed, which scales the parameter of the estimation by allowing the kernel width to vary based upon the distance from $X_i$ to the k-th nearest neighbor in the set comprising N−1 points. For instance, the modified kernel method may be expressed as:

$$f(x) = \frac{1}{N} + \sum_{i=1}^{N} \frac{1}{\max_{(h,d_i;k)}} K\left(\frac{x - X_i}{\max_{(h,d_i;k)}}\right)$$

Here, the window width of the kernel placed on the point Xi is proportional to di,k (where di,k is the distance from the i-th sample to the k-th nearest neighbor) so that data points in regions where the data is sparse will have flatter kernels, and h is the minimum allowed kernel width.

Optionally, the Epanechnikov kernel is utilized:

$$K(u) = \tfrac{3}{4}(1 - u^2) 11_{(\|u\| \leq 1)}$$

where the function $1(\|u\| \leq 1)$ evaluates to 1 if the inequality is true and zero for all other cases.

Along with the various geospatial display capabilities, according to certain embodiments, the present system and method optionally provides clustering based on spatial statistics. In order to group data based on spatially similar population statistics, in one embodiment a multidirectional optimum ecotope-based algorithm ("AMOEBA") is used for creating spatial weights matrix developed. This procedure is designed to identify hot and cold spots in mapped data by assessing the spatial association of a particular mapped unit to its surrounding units. It aids in the demarcation of clusters of related spatial units, and this is utilized to group counties and other geographic areas based on population statistics.

In particular, AMOEBA maps clusters of high and low values by creating a spatial weights matrix based on the Getis-Ord $G^*_i$. For a given location i, $G^*_i$ is defined as:

$$G^*_i = \frac{\sum_{j=1}^{N} w_{ij} x_j - \bar{x} \sum_{j=1}^{N} w_{ij}}{S\sqrt{\frac{[\sum n_{j=1} w_{ij}^2 - (\sum n_{j=1} w_{ij})^2]}{N-1}}}$$

where the number of spatial units, $x_j$ is the value of interest within the area unit at location j, $\bar{x}$ is the mean of all values, and $$s = \sqrt{\frac{\sum_{j=1}^{N} x_j^2}{N} - (\bar{x}^2)}$$

$w_{ij}$ is used as an indicator function that is one if j is a neighbor of i and zero otherwise.

Figure 5:
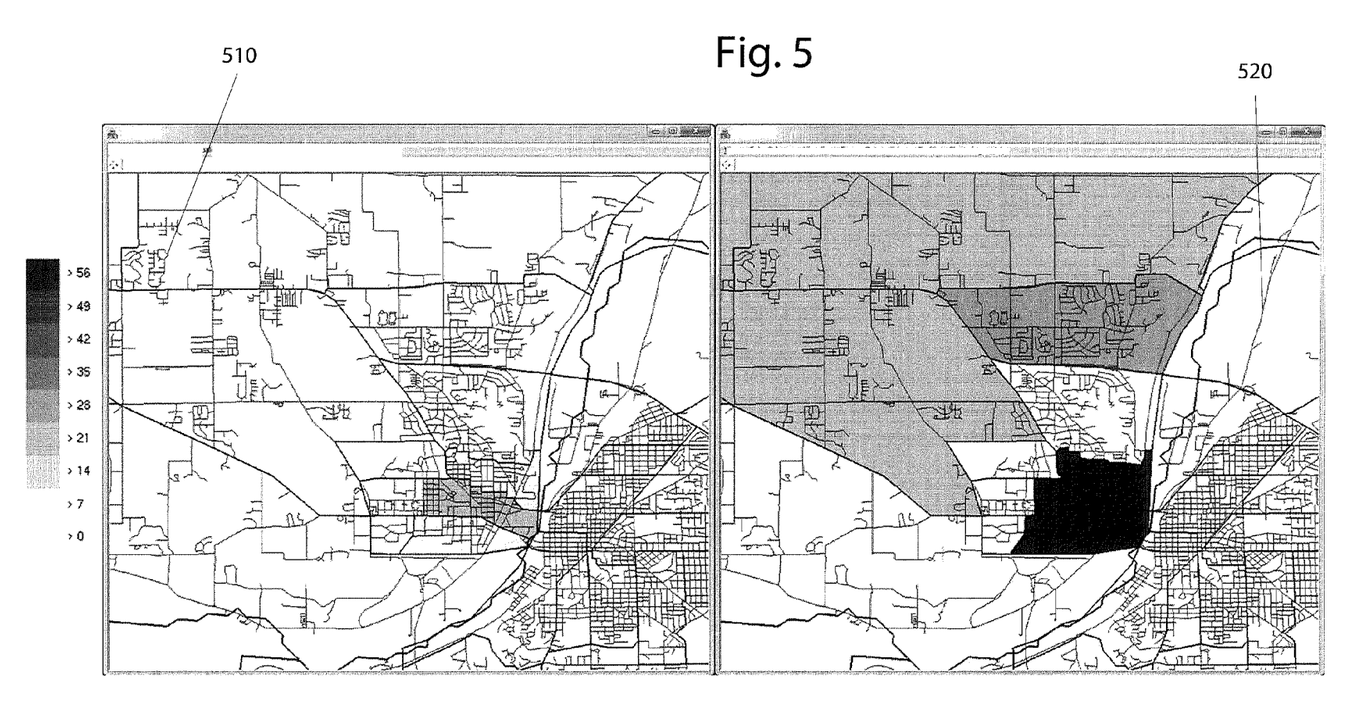
FIG. 5 shows an exemplary display generated by the visual analytics system according to one embodiment.

The AMOEBA algorithm develops a cluster from a selected seed location by evaluating $G^*_i$ at all locations surrounding this seed location, and if the addition of a neighbor to the cluster increases the $G^*_I$ value, then the neighbor is added. FIG. 5 illustrates the application of AMOEBA clustering according to at least one embodiment. Specifically, FIG. 6 shows two comparative views of the geospatial rendition of temporal data 400, with view 510 establishing a choropleth map of vandalism counts in West Lafayette, Ind., and view 520 showing the results of an AMOEBA clustering.

Groups are colored based on their $G^*_i$ values, and census tracts that connect to other census tracts of the same color are considered to be a cluster.

In general, visual analytics arrangement 100 displays information regarding public health in a manner that provides for intuitive analysis, using geospatial and/or temporal maps. Geospatial and/or temporal maps provide a geographical map of an area of interest, and may provide glyphs or other visual symbols to indicate locations, timing, and/or frequency of phenomena. In accordance with this embodiment of the present invention, the arrangement 100 provides, among other things, a geospatial and/or temporal map that shows the number and location of incidences with selected crime and/or health and safety occurrences reported in CTC data source 108. Additional details regarding the displays generated by the arrangement 100 are provided further below.

Figure 2:
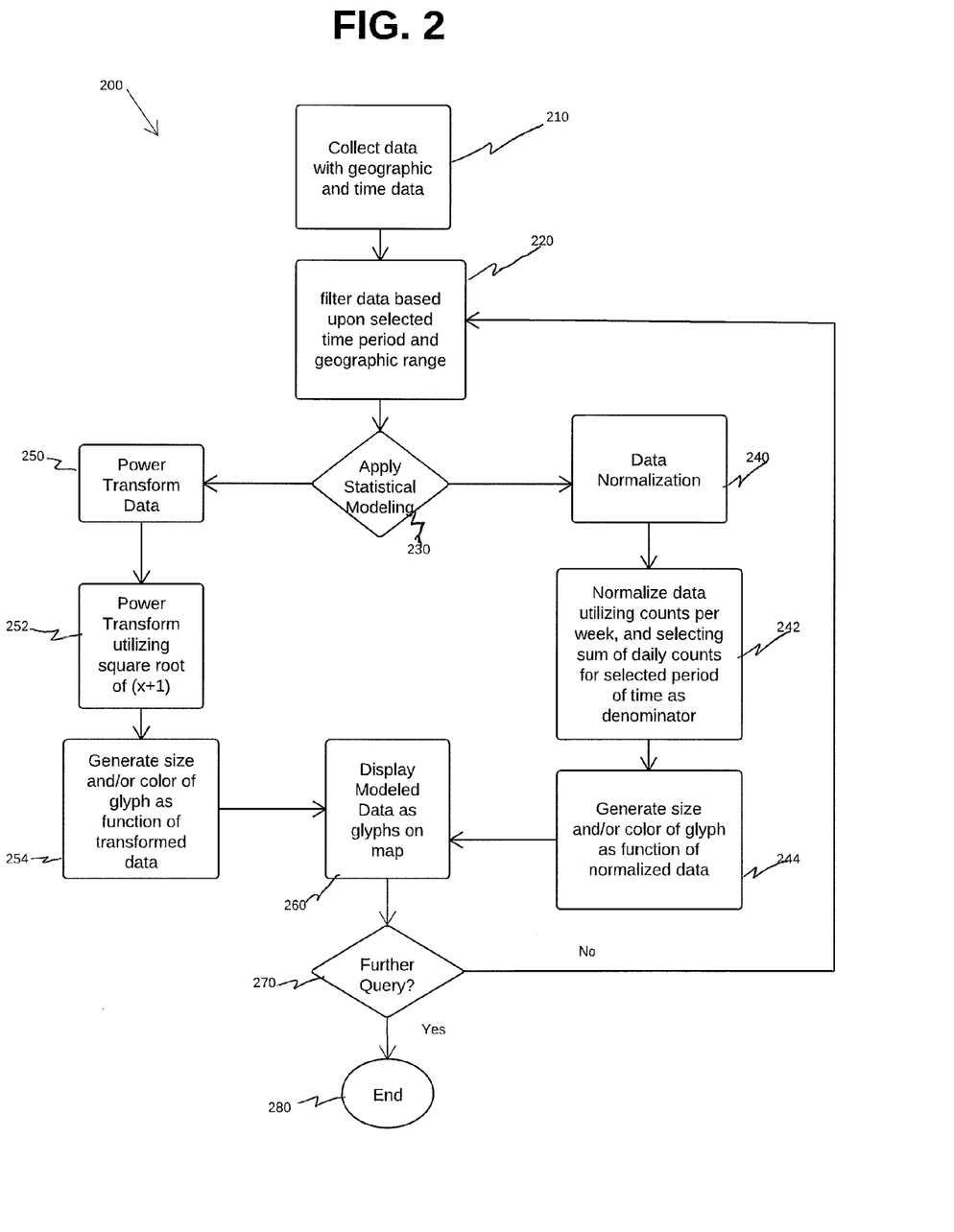
FIG. 2 shows a flow diagram of an exemplary set of operations that may be carried out by a computing device to generate a geospatial and/or temporal display of the visual analytics arrangement of FIG. 1.

FIG. 2 shows an exemplary embodiment of a method for analyzing geospatial and/or temporal data display utilizing a visual analytics arrangement. According to at least one embodiment, the method for analyzing geospatial and/or temporal data 200 includes the steps of: collecting CTC data 210; filtering that data based upon selected parameters 220; applying statistical modeling 230 to the data based upon the selected time period and geographic range; and displaying the modeled data as glyphs on a geographic display such as a map 260.

According to at least one embodiment, the step of applying statistical modeling 230 includes the use of logarithm or power transformation, such as a power transformation step 250. Further, according to at least one embodiment, the use of a logarithm or power transformation includes a step 252 of performing a power transform utilizing the square root of (x+1) for a given time period and geographic range. Similarly, depending upon the data supplied, the log(x+1) or a simple square root transformation could be utilized, depending upon the variability of the data. Upon applying the power transformation or logarithm, visual analytics arrangement 100 performs step 254 of generating a glyph having a size and/or color driven by the function of the transformed data. Thereafter, the statistically modeled data is displayed to a user via visual analytics arrangement 100 by displaying the glyphs generated in step 254 on a map in the geographic location associated with the data 260.

According to at least one other embodiment, the step of applying statistical modeling 230 includes the use of data normalization as shown in step 240. According to at least one embodiment, step 240 of normalizing data is performed, for example, to reduce the variation caused by seasonal effects and increases in data collection capacity. According to at least one embodiment, step 240 of normalizing data may include step 242 of utilizing counts per week for each of one or more particular locations to compensate for different scaling in counts over time. Further, according to at least one embodiment, generating a normalized value for each of one or more locations is performed by dividing the total value for each of the plurality of locations by a total number of reported CTC incidences for a corresponding site over a time window. By way of nonlimiting example, the denominator of such a normalization in step 242 utilizes the sum of the daily counts for the past month, two months, three months, four months, five months, six months, seven months, eight months, nine months, ten months, eleven months, or year. The use of a sliding window normalizing data utilizing counts per week allows observation of seasonal effects and larger trends while removing smaller aberrations and intra-week sampling effects. However, it will be appreciated that such a sliding window normalization will not be utilized when a user wishes to observe short-term effects.

According to at least one exemplary embodiment, upon performing data normalization through steps 240 and 242, in step 244 the normalized data is utilized to generate glyphs of a size and/or color as a function of the normalized data generated in steps 240 and 242. Thereafter, in step 260, the generated glyphs are displayed to a user via visual analytics arrangement 100 on a map in the geographic location associated with the data.

Upon review of the glyphs generated and displayed on the map in step 260, in step 270, a user evaluates the display to determine whether the generated display is acceptable for the user's evaluative purposes, or whether further querying would be preferred. If the display provides the requisite information needed for the user's evaluative purposes, the user may utilize the display as generated, and may print, save, or otherwise share, either physically or digitally, the results with colleagues for reporting purposes, for generating discussion on the findings, or for other uses. However, should the display fail to provide the requisite information, should another time period or evaluative method be needed, or should the results cause the user to determine that additional querying is necessary, the user may re-start the method for analyzing geospatial and/or temporal data display 200 from any of the prior steps such as step 210 of collecting additional data, step 220 of filtering the data based upon a selected time period and geographic range 220, step 230 of applying statistical modeling, or any other step deemed necessary by the user.

Figure 3:
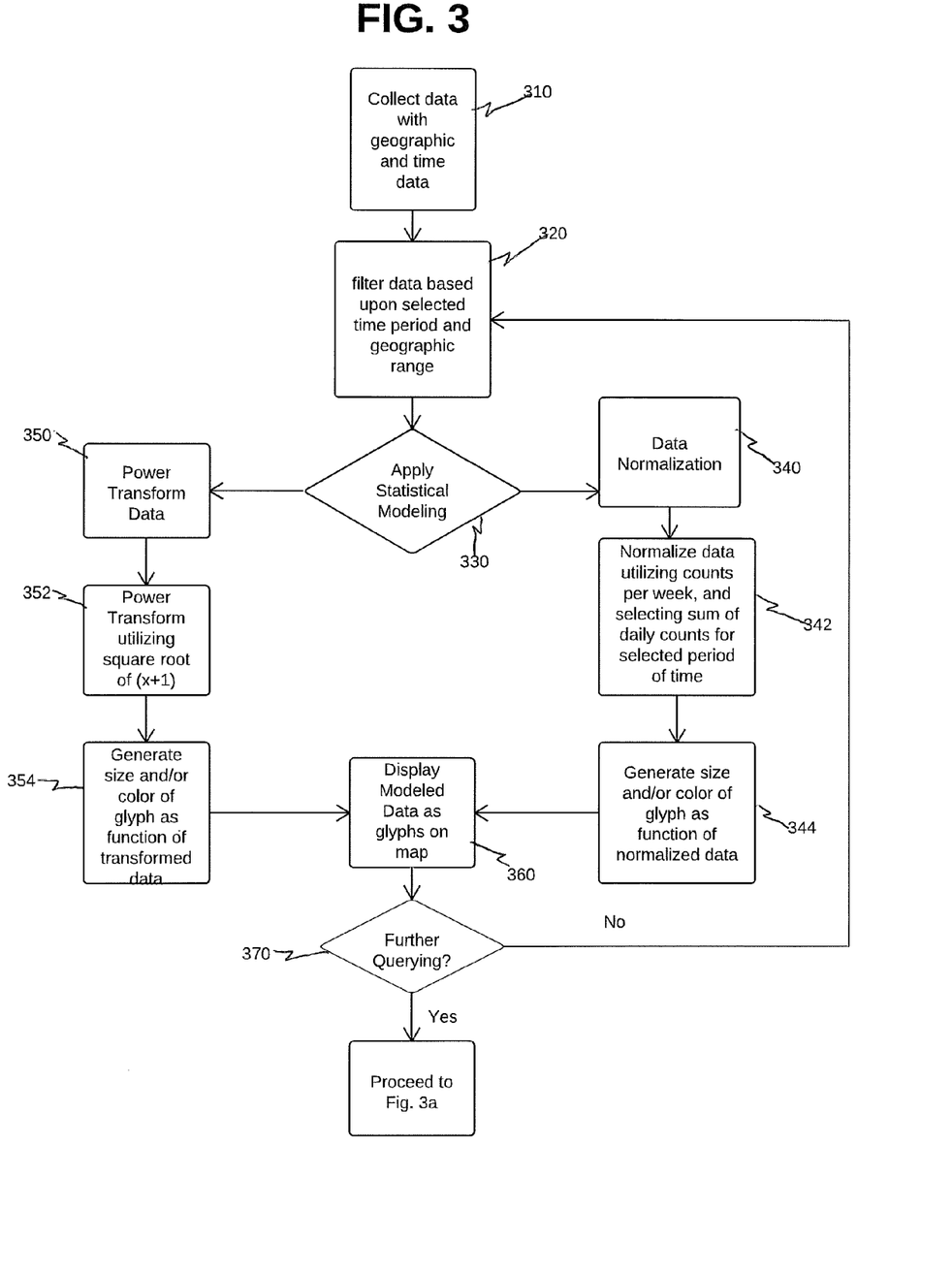
FIGS. 3 and 3a shows a flow diagram of an exemplary set of operations that may be carried out by a computing device to generate a refined analysis of the raw geospatial and/or temporal display of the visual analytics arrangement of FIG. 1.
Figure 3A:
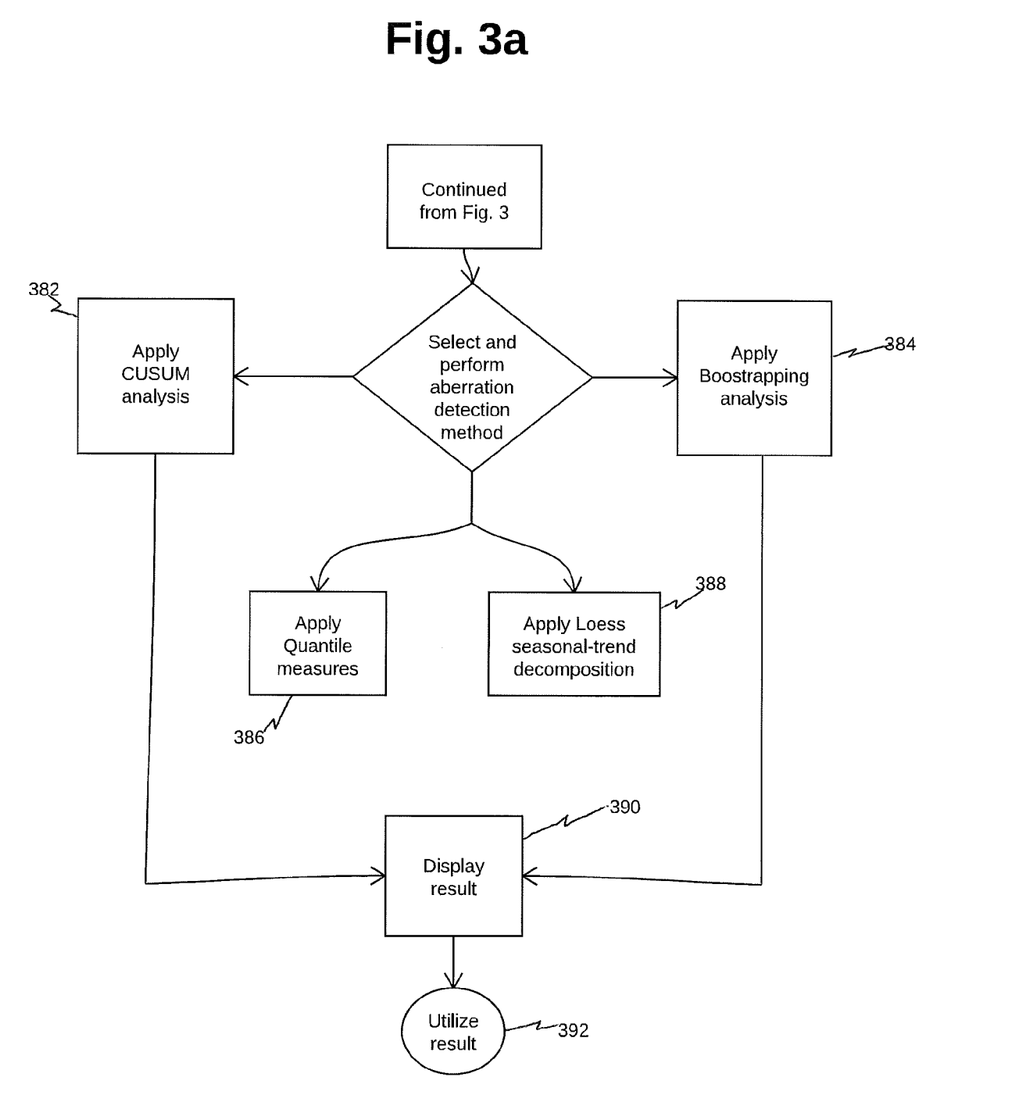

Turning now to FIGS. 3 and 3a, according to at least one exemplary embodiment of a method for analyzing geospatial and/or temporal data display utilizing a visual analytics arrangement 300, including the steps of: collecting CTC data 310; filtering that CTC data based upon selected parameters 320; applying statistical modeling 330 to the CTC data based upon the selected time period and geographic range; and displaying the modeled data as glyphs on a geographic display such as a map 360.

According to at least one embodiment, the step of applying statistical modeling 330 includes the use of logarithm or power transformation, such as a power transformation step 350. Further, according to at least one embodiment, the use of a logarithm or power transformation includes a step 352 of performing a power transform utilizing the square root of (x+1) for a given time period and geographic range. Similarly, depending upon the data supplied, the log(x+1) or a simple square root transformation could be utilized, depending upon the variability of the data. Upon applying the power transformation or logarithm, visual analytics arrangement 100 performs step 354 of generating a glyph having a size and/or color driven by the function of the transformed data. Thereafter, in step 360, the statistically modeled data is displayed to a user via visual analytics arrangement 100 by displaying the glyphs generated in step 354 on a map in the geographic location associated with the data 360.

According to at least one other embodiment, the step of applying statistical modeling 330 includes the use of data normalization as shown in step 340. According to at least one embodiment, step 340 of normalizing data is performed, for example, to reduce variation and data noise. According to at least one embodiment, step 240 of normalizing data may include step 342 of utilizing counts per week for each of one or more particular locations to compensate for different scaling in counts over time. Further, according to at least one embodiment, generating a normalized value for each of one or more locations is performed by dividing the total value for each of the plurality of locations by a total number of reported CTC incidences for a corresponding site over a time window. By way of nonlimiting example, the denominator of such a normalization in step 342 utilizes a sum of the daily counts for the past month, two months, three months, four months, five months, six months, seven months, eight months, nine months, ten months, eleven months, or year for such normalization. The use of a sliding window normalizing data utilizing counts per week allows observation of seasonal effects and larger trends while removing smaller aberrations and intra-week sampling effects. However, it will be appreciated that such a sliding window normalization will not be utilized when a user wishes to observe short-term effects.

Upon performing data normalization through steps 340 and 342, in step 344, the normalized data is utilized to generate glyphs of a size and/or color as a function of the normalized data generated in steps 340 and 342. Thereafter, in step 360, the generated glyphs are displayed to a user via visual analytics arrangement 100 on a map in the geographic location associated with the data.

Upon review of the glyphs generated and displayed on the map in step 360, in step 370, a user evaluates the display to determine whether the generated display is acceptable for the user's evaluative purposes, or whether further querying would be preferred. If the display provides the requisite information needed for the user's evaluative purposes, the user may utilize the display as generated, and may print, save, or otherwise share, either physically or digitally, the results with colleagues for reporting purposes, for generating discussion on the findings, or for other uses. However, should the display fail to provide the requisite information, should another time period or evaluative method be needed, or should the results cause the user to determine that additional querying is necessary, the user may re-start the method for analyzing geospatial and/or temporal data display 300 from any of the prior steps such as step 310 of collecting additional data, step 320 of filtering the data based upon a selected time period and geographic range 320, step 330 of applying statistical modeling, or any other step deemed necessary by the user.

According to at least one embodiment, in at least one additional step, once a user is satisfied with the results of the statistically modeled data, or in lieu of utilizing the statistically modeled data a user may select and perform at least one aberration detection method in step 380.

According to at least one embodiment, a user may utilize the step of performing a CUSUM analysis for the at least one aberration detection method as shown in step 382. For purposes of this nonlimiting example, CUSUM is defined as:

$$S_t = \max\left(0, S_{t-1} + \frac{x_t(\mu_0 + k\sigma_{x_1})}{\sigma_{x_1}}\right)$$

where $S_t$ is the current CUSUM, $S_{t-1}$ is the previous CUSUM, $X_t$ is the count at the current time, $\mu_0$ is the expected value, $\sigma_{X_t}$ is the standard deviation, and k is the detectable shift from the mean. $\mu_0$ and $\sigma_{X_t}$ are computed according to the degree of sensitivity. According to at least one embodiment, a user may define three different models (C1, C2, C3), with each model utilizing different time period for the $\mu_0$ and $\sigma_{X_t}$ computations. By way of nonlimiting example, C1 is the baseline period is $Day_{-7}, \ldots, Day_{-1}$ and a flag is noted on $Day_0$. Further, by way of nonlimiting example, C2 uses $Day_{-9}, \ldots, Day_{-3}$ as the baseline, and C3 uses $Day_{-9}, \ldots, Day_{-3}$ as the baseline. Further, according to at least one embodiment, an average of $Day_{-2}, \ldots, Day_0$ is used to detect the aberration. It will be appreciated that in at least one embodiment, in the event that the CTC data has a relatively small number of counts, doubled baselines may be utilized in order to avoid zero count for the baseline period.

According to at least one embodiment, a user may utilize the step of performing a bootstrapping analysis for the at least one aberration detection method as shown in step 384. It will be appreciated that bootstrapping is a general-purpose robust alternative to parametric inference used when the analyst does not wish to make strong parametric assumptions about the data. According to at least one embodiment, bootstrapping involves the sampling of data with replacement in order to simulate the distribution of the data and functions thereof. According to at least one nonlimiting example a user applying bootstrapping to dependent data will preserve as much of the dependence structure as possible when doing the resampling, typically through a blocked approach.

It will be appreciated that the step of applying bootstrapping analysis 384 is computationally intensive, but, according to at least one embodiment, may be employed in a straightforward manner. Specifically, according to one exemplary embodiment, to obtain R null replicates of the statistic, resampling R windows of length $t_w$ days corresponding to null data and computing the statistic may result in bootstrap replicates $S_t^{(1)}, S_t^{(2)}, \ldots, S_t^{(R)}$. According to at least one embodiment, in prospective mode, the null data occurs prior to the window under investigation; in retrospective mode, one may opt to include data from after the window as well. According to at least one embodiment, the bootstrap significance associated with S* is then $$p_t = (1 + \text{number of} \{S_t^{(i)}\} \text{exceeding } S_t^*)/(1+R)$$

If the mild assumptions underlying the bootstrap hold, the nun distribution of $p_t$ is approximately discrete uniform over $\{1/R, 2/R, \ldots, R/R\}$. Consequently, if there is no signal in the window under investigation, rejecting the null hypothesis when $p_t^* \leq \alpha$ will result in a false alarm rate of $\alpha \times 100\%$. According to at least one embodiment, in prospective mode, a system may update pt with the passage of time, and in this case a plot of $p_t^*$ versus $_t$ may be appropriate. In this case the $\{p_t\}$ are themselves correlated; moreover, the probability of at least one false alarm grows with $_t$ for fixed $\alpha$. If the number of null windows is less than R (common for our analyses), then bootstrapping is unnecessary when only a p-value is required, since the bootstrap p-value will have expectation equal to the fraction of null windows with statistic at least as extreme as the observed value.

According to at least one embodiment, a user may utilize the step of performing a quantile measures for the at least one aberration detection method as shown in step 386. By way of nonlimiting example quantile measures may be utilized to detect unusual variation in data when operating in retrospective mode. According to at least one embodiment, quantile measures may be performed by selecting all data within a radius of incidence, identifying all encounters over a time window of $t_w$ days after the alleged release at time t. Over the window $[t, (t+t_w)]$, there is a distance to the epicenter associated with each encounter, and the detection statistic $S^*_t$ is the radius inside which x % of the window's cases occur. As such, quantile measurement operates on the theory that an adverse event near the epicenter will cause the distribution of these distances to be shifted downward, and this particular aberration detection method utilizes this theory detect such shifts over time.

Yet another aberration detection method includes seasonal-trend decomposition based on loess, as shown in step 388. Such an aberration detection method results in signal correlation. By way of nonlimiting example, time series signals may be viewed as the sum of multiple trend components: a seasonal component and remainders. According to at least one embodiment, for each data signal, "trend components" are extracted to represent the long term trend and yearly seasonality using a seasonal decomposition of time series by loess ("STL"). In such an example, the "seasonal component" would represent the day-of-the-week effect as expressed in the following equation:

$$Y_{it} = T_{it} + S_{it} + D_{it} + r_{it}$$

where for the ith series, $Y_{it}$ is the original series, $T_{it}$ is the long term trend, $S_{it}$ is the yearly seasonality, $D_{it}$ is the day-of-the-week effect, and $r_{it}$ is the remainder. Such an exemplary example allows the correlation between the extracted components to be analyzed for any potential effects on one another.

According to at least one embodiment, after the step of selecting and performing aberration detection methods has been utilized, the generated data is visually displayed to a user via visual analytics arrangement 100 in step 390. Upon review of the data generated and displayed in step 390, according to at least one embodiment, a user can evaluate the display to determine whether the generated display is acceptable for the user's evaluative purposes. If the display provides the requisite information needed for the user's evaluative purposes, the user may utilize the display as generated, and may print, save, or otherwise share, either physically or digitally, the results with colleagues for reporting purposes or for generating discussion on the findings. However, should the display fail to provide the requisite information, or should another time period or evaluative method be needed, the user may re-start the method for analyzing geospatial and/or temporal data display 300 from any of the prior steps and/or may change the parameters, statistical modeling methods, and/or aberration detection steps to reach a desired outcome.

It will be appreciated that the above-described embodiments are merely exemplary, and that those of ordinary skill in the art may readily devise their own implementations that incorporate the principles of the present invention and fall within the spirit and scope thereof.

What is claimed is:

1. A method comprising:
obtaining first data regarding criminal, traffic and/or civil incidents, the first data comprising reported criminal, traffic and/or civil incidents from a plurality of locations;
sorting the first data based upon incident categories;
applying seasonal trend decomposition with loess smoothing for the first data;
plotting incidents within the first data as points, density estimated heatmaps, or chloropleth maps for a defined geotemporal unit;
displaying the plotted incidents to a user via a graphic user interface;
obtaining second data regarding demographic data, weather data, or special events data, the second data comprising data related to a plurality of locations;
filtering the first data based upon the correlation of the first data with the second data; and
predicting the occurrence of additional incidents based upon the filtered data.

2. A method comprising:
obtaining first data regarding criminal, traffic and/or civil incidents, the first data comprising reported criminal, traffic and/or civil incidents from a plurality of locations;
sorting the first data based upon incident categories;
applying seasonal trend decomposition with loess smoothing for the first data;
plotting incidents within the first data as points, density estimated heatmaps, or chloropleth maps for a defined geotemporal unit; and
displaying the plotted incidents to a user via a graphic user interface,
wherein plotting the incidents within the first data is performed as a density estimated heatmap, wherein the density estimated heatmap is performed by employing a variable kernel method which scales the parameter of an estimation by allowing a kernel width to vary according to the algorithm $$f(x) = \frac{1}{N} + \sum_{i=1}^{N} \frac{1}{\max_{(h,d_i,k)}} K\left(\frac{x - X_i}{\max_{(h,d_i,k)}}\right).$$

3. The method of claim 2, further comprising generating display information based on the density estimated heatmap.

4. The method of claim 1, further comprising plotting spatial statistics of the first data utilizing a multidirectional optimum ectope-based algorithm to create a spatial weights matrix to identify hot and cold spots in mapped data.

5. The method of claim 1, further comprising:
generating quantile measures based on a select epicenter and time window;
displaying information representative of the quantile measures.

6. The method of claim 2, further comprising obtaining second data regarding demographic data, weather data, or special events data, the second data comprising data related to a plurality of locations.

7. The method of claim 6, further comprising:
filtering the first data based upon the correlation of the first data with the second data.

8. The method of claim 7, further comprising predicting the occurrence of additional incidents based upon the filtered data.

9. A method comprising:
obtaining first data regarding criminal, traffic and/or civil incidents, the first data comprising reported criminal, traffic and/or civil incidents from a plurality of locations;
sorting the first data based upon incident categories;
applying seasonal trend decomposition with loess smoothing only for the first data;
plotting incidents within the first data as points, density estimated heatmaps, or chloropleth maps for a defined geotemporal unit;
obtaining second data regarding demographic data, weather data, or special events data, the second data comprising data related to a plurality of locations; and
displaying the plotted incidents and second data to a user via a graphic user interface.

10. The method of claim 9, further comprising:
generating quantile measures based on a select epicenter and time window;
displaying information representative of the quantile measures.

11. A method comprising:
obtaining first data regarding criminal, traffic and/or civil incidents, the first data comprising reported criminal, traffic and/or civil incidents from a plurality of locations;
sorting the first data based upon incident categories;
applying seasonal trend decomposition with loess smoothing for the first data; plotting incidents within the first data as points, density estimated heatmaps, or chloropleth maps for a defined geotemporal unit;
obtaining second data regarding demographic data, weather data, or special events data, the second data comprising data related to a plurality of locations; and
displaying the plotted incidents and second data to a user via a graphic user interface,
wherein plotting the incidents within the first data is performed as a density estimated heatmap, wherein the density estimated heatmap is performed by employing a variable kernel method which scales the parameter of an estimation by allowing a kernel width to vary according to the algorithm $$f(x) = \frac{1}{N} + \sum_{i=1}^{N} \frac{1}{\max_{(h,d_i,k)}} K\left(\frac{x - X_i}{\max_{(h,d_i,k)}}\right).$$

12. The method of claim 11, wherein generating the heatmap includes displaying a color of the glyph based on the value for the site.

13. The method of claim 9, further comprising plotting spatial statistics of the first data utilizing a multidirectional optimum ectope-based algorithm to create a spatial weights matrix to identify hot and cold spots in mapped data.

14. The method of claim 13, wherein the spatial weights matrix is determined according to the value of $G^*_i$, where $G^*_i$ is defined as:

$$G_i^* = \frac{\sum_{j=1}^{N} w_{ij} x_j - \bar{x} \sum_{j=1}^{N} w_{ij}}{S \sqrt{\frac{[\sum n_{j=1} w_{ij}^2 - (\sum n_{j=1} w_{ij})^2]}{N-1}}}.$$

15. The method of claim 14, further comprising: displaying a color of a group based on the $G^*_i$ value.

* * * * *